United States Patent
Östvold

(10) Patent No.: US 9,150,775 B2
(45) Date of Patent: Oct. 6, 2015

(54) METHOD FOR WATER TIGHTENING OF WATER BEARING ZONES AND STABILIZATION OF SAND IN UNDERGROUND CONSTRUCTIONS

(75) Inventor: Terje Östvold, Trondheim (NO)

(73) Assignee: TEMASI AS, Fornebu (NO)

(*) Notice: Subject to any disclaimer, the term of this patent is extended or adjusted under 35 U.S.C. 154(b) by 107 days.

(21) Appl. No.: 13/515,003

(22) PCT Filed: Dec. 20, 2010

(86) PCT No.: PCT/NO2010/000479
§ 371 (c)(1),
(2), (4) Date: Jun. 11, 2012

(87) PCT Pub. No.: WO2011/078690
PCT Pub. Date: Jun. 30, 2011

(65) Prior Publication Data
US 2012/0269584 A1    Oct. 25, 2012

(30) Foreign Application Priority Data
Dec. 21, 2009    (NO) .................................. 20093567

(51) Int. Cl.
*E02D 3/12*    (2006.01)
*C09K 8/575*    (2006.01)
(Continued)

(52) U.S. Cl.
CPC ............. *C09K 8/5758* (2013.01); *C09K 8/5045* (2013.01); *C09K 8/514* (2013.01); *C09K 8/572* (2013.01); *C12Y 305/01005* (2013.01); *E02D 3/12* (2013.01)

(58) Field of Classification Search
CPC ...... C09K 8/5045; C09K 8/514; C09K 8/572; C09K 8/5758; C12Y 305/01005; E02D 3/12
USPC .................... 405/264; 166/276, 293–294, 300
See application file for complete search history.

(56) References Cited

U.S. PATENT DOCUMENTS

| | | | |
|---|---|---|---|
| 4,002,204 A | | 1/1977 | Cavin |
| 4,753,882 A * | | 6/1988 | Takashio et al. .............. 435/228 |
| 2007/0204990 A1 * | | 9/2007 | Kotlar et al. ................... 166/276 |

FOREIGN PATENT DOCUMENTS

| | | |
|---|---|---|
| EP | 1980604 | 10/2008 |
| WO | WO9800530 A1 | 1/1998 |

(Continued)

OTHER PUBLICATIONS

Howell, Stacey et al.; The Specific Effects of Buffers Upon Urease Activity; Jan. 1934; All pages.*

(Continued)

*Primary Examiner* — Benjamin Fiorello
(74) *Attorney, Agent, or Firm* — Alix, Yale & Ristas, LLP

(57) ABSTRACT

Method for water tightening of water bearing zones and stabilization of sand in underground constructions, by precipitation of at least one mineral, by introducing into the construction, at the least one aqueous solution of salts comprising $Ca^{2+}$ ions and urea, and an urease. The urease may be plant based, and made by grounding the plant wherefrom the urease is based, adding water, and soaking at occasional stirring between 2 and 20 h at room temperature. Then the achieved solution is filtrated, and the filtrate is lyophilized. The urease may also be biotechnologically produced by bacteria in an aqueous solution, where after the achieved solution is filtrated, and the filtrate is lyophilized.

6 Claims, 2 Drawing Sheets

Precipitation of $CaCO_3$ from 1S QNC solution(Urea and $Ca^{2+}$ concentrations in the order of = 1-0.5 mole/l + extract from 10g beans/l solution). The effect of extract of different bean meals at room temperature.

(51) Int. Cl.
*C09K 8/504* (2006.01)
*C09K 8/514* (2006.01)
*C09K 8/57* (2006.01)

(56) References Cited

FOREIGN PATENT DOCUMENTS

| WO | WO9905394 A1 | 2/1999 |
| WO | WO2005124100 A1 | 12/2005 |
| WO | WO2007064213 A1 | 6/2007 |

OTHER PUBLICATIONS

Yung-Hua Li, et al.; Regulation of urease gene expression by *Streptococcus salivarius* growing in biofilms; Center for Oral Biology and Department of Microbiology and Immunology, University of Rochester School of Medicine and Dentistry; 2000.*

Chernov, N. E. et al., "Freeze Drying of Urease", Khimiko-Farmatsevticheskii Zhurnal, 1983, vol. 17, No. 1, pp. 109-112 (abstract).

International Search Report dated Mar. 8, 2011.

* cited by examiner

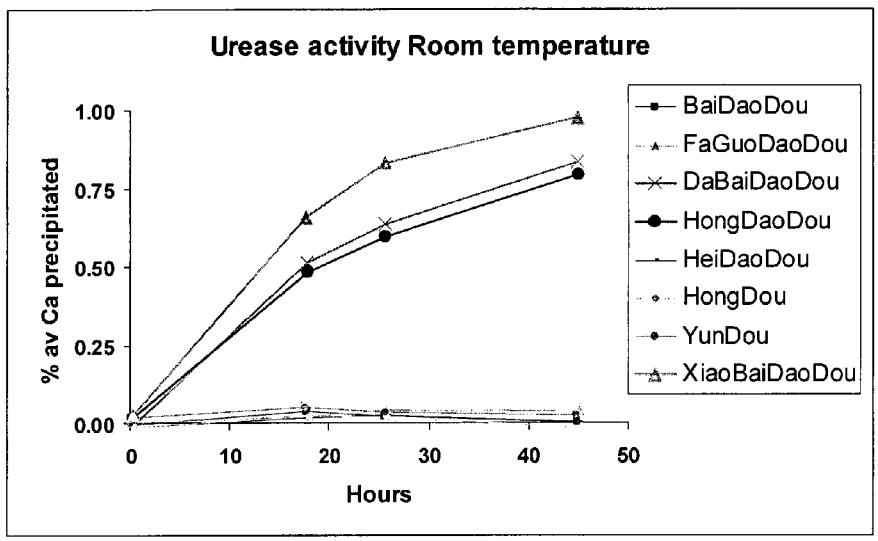
Fig. 1  Precipitation of $CaCO_3$ from 1S QNC solution (Urea and $Ca^{2+}$ concentrations in the order of = 1-0.5 mole/l + extract from 10g beans/l solution). The effect of extract of different bean meals at room temperature.
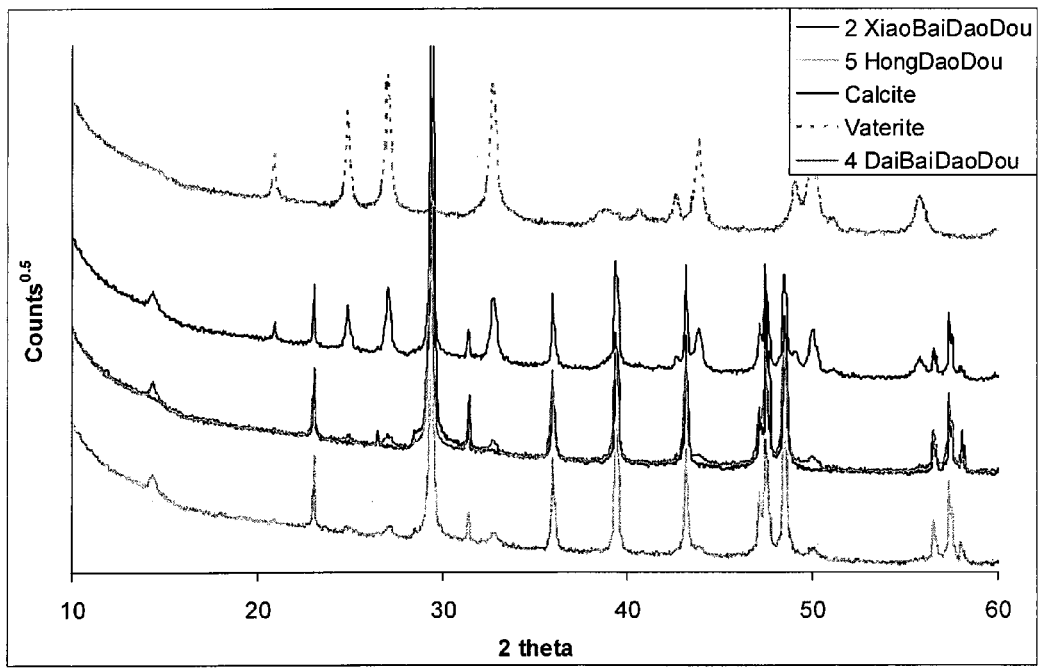
Fig. 2  XRD of the precipitate from the urease active beans, as well as spectra from powders containing

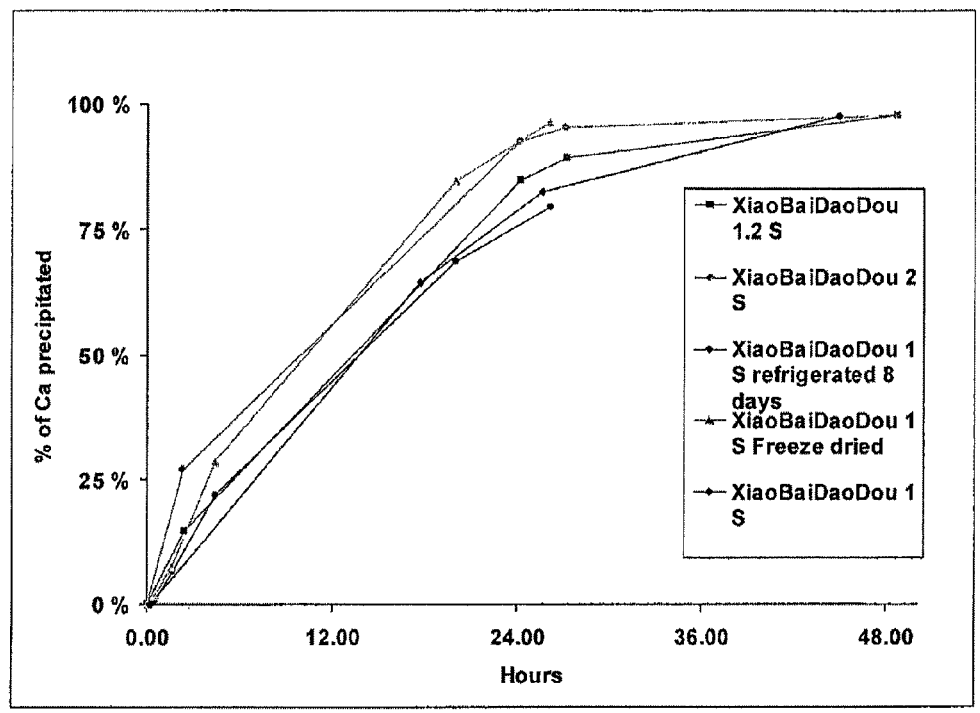
Fig. 3  Relative urease activity in various preparations of QNC solutions. 1S of calcium and urea was used. The concentraions of the bean meal solution was varied. The orange triangles show the activity of a 1S solution of freeze dried solution 8 days after the solution was first made.

METHOD FOR WATER TIGHTENING OF WATER BEARING ZONES AND STABILIZATION OF SAND IN UNDERGROUND CONSTRUCTIONS

The present invention relates to a method for water tightening of water bearing zones and stabilization of sand in underground constructions such as water bearing zones of oil field reservoirs, by precipitation of at least one mineral according to the preamble of the independent claim.

BACKGROUND

Consolidation of oil reservoirs is known, but sand production from a weak or badly consolidated oil reservoir is still a serious problem that causes damage to the reservoir itself, wells, pumps etc. It may also be very costly to remove sand from the oil phase at a later stage in the oil recovery process. Water proofing technology used to reduce water production from special zones into oil field wells in order to obtain enhanced oil recovery is also an important issue for oil field operations.

U.S. Pat. No. 5,143,155 mentions use of urease manufactured from bacteria in situ, to reduce porosity and permeability of oil reservoirs, by precipitating $CaCO_3$ from an aqueous solution containing calcium chloride and urea. The object of this US patent is to reduce porosity/permeability of geological subterranean formations to increase oil production from an oil reservoir and to reduce the flow of contaminations from previous operation present in the aqueous phase.

It is taught in SPE publications 50621 (Harris, R. E. and McKay, I. D. New application for enzymes in oil and gas production. The 1998 SPE European Petroleum Conference, The Hague, The Netherlands 20-22 Oct. 1998) that urease may be used to decompose urea to consolidate sand when precipitating $CaCO_3$. It is also mentioned in this publication that calcium phosphate can be produced in a reaction between an enzymatically decomposed phosphate and calcium chloride. The publication concludes that such materials have a potential for sealing water conveying layers and for applications related to sand stabilizing.

The Norwegian patent 326444 describes chemical consolidation of sandy oil formations and water tightening of underground constructions using calcium phosphate or calcium carbonate, and urease from a plant.

From U.S. Pat. Nos. 5,143,155 and No. 6,401,819 B1 and the SPE publication 50621 (Harris, R. E. and McKay, I. D. New application for enzymes in oil and gas production. The 1998 SPE European Petroleum Conference, The Hague, The Netherlands 20-22 Oct. 1998) it is known that $CaCO_3$ precipitation in oil reservoirs through an enzymatic process using urease, a $Ca^{2+}$ source and urea can improve the formation stability and reduce sand production. It is also known that calcium, urea and urease can form $CaCO_3$ in order to change the porosity and permeability in porous media. See eg. Nemati, M., Greene, E. A. og Voordouw. G. Permeability profile modification using bacterially formed calcium carbonate: comparison with enzymic option. Process Biochemistry 40 (2005) 925-933, and Nemati, M. and Voordouw. Modification of permeability profile, using calcium carbonate produced enzymatically in situ. Enzyme and Microbial Technology 33 (2003) 635-642.

The technological process of performing the well and water tightening treatments, in order to reach the objects stated for oil field- and underground water tightening treatments in large scale is, however, not explained in the above patents and publications in such details that the processes can be done in an economic industrial process. The major problem is the supply of urease in sufficient quantities and in a stable form.

Freeze dried or lyophilized urease is a commercial product, one can buy it from for instance Merck or Sigma. However, these ureases are produced in such a way that they do not function for consolidation, and they are very expensive (about NOK 260.000, for 1 kg). It has not been possible for the applicant to get hold of the methods the manufacturers are using, but it is likely to assume that certain stabilizers have been added to the aqueous solution before lyophilization, and that these stabilizers are the reasons why the urease does not work for consolidation.

OBJECT

The main object of the invention is to provide urease in a stable form, and in a form being possible to transport and store in larger quantities, in order to carry out sand stabilization in oil field reservoirs and reduce water production in oil field wells and/or water tightening of underground constructions. Another object is that the urease should be produced in large quantities and to a reasonable price.

INVENTION

The objects of the invention are reached by a method for water tightening of water bearing zones and stabilization of sand in underground constructions, by introducing an aqueous salt solution comprising $Ca^{2+}$ ions, urease and urea into said zones and constructions to precipitate at least one mineral.

The novel and inventive by the method for reaching the objects is to provide the urease in a solid form by directly lyophilize a water based urease solution. This is of significant importance because transportation to the site of use is expensive and further because urease is unstable in aqueous solutions. The process for introducing aqueous solutions into the constructions to be treated, and the precipitation of salts giving the desired result is described in prior art, e.g. NO 326444 or NO 313203 and thus obvious to a person skilled of the art. By "stable" it is, in this application, meant that the urease can remain chemically unchanged for at least a year stored correctly, and by "unstable" it is meant that the urease will alter within 14 days.

The urease must be originated from a rich and/or available source, in order to produce urease in very large quantities at a reasonable price. Examples of such sources are plants, preferably beans, or biotechnologically by using bacteria. The source to be used must be urease active, and must have a $CaCO_3$ precipitation activity, see FIG. 1, and the type of $CaCO_3$ should be as given in FIG. 2, being mainly Calcite. It is observed in lab experiments that many commercially available urease qualities do not give sufficient $CaCO_3$ for sand stabilization, even if the urease is very efficient in breaking down urea. This is the one of the important reasons why the beans are extracted in water.

Urease may also be produced biotechnologically by using bacteria, possibly gene manipulated bacteria, according to known technology. Biotechnologically produced urease should be produced in water with additives only compatible with the $CaCO_3(s)$ precipitation process being a result of this invention. The urease produced from known bacteria are cytoplasmic (intracellular), apart from *Heliobacter pylori*, but also this bacteria can produce urease inside its cell membrane. Using gene manipulated bacteria the urease may be released directly to the surrounding solution, and filtrated from the bacteria which are substantially larger. In cases where interiorly producing bacteria are used, the method according to the present invention opens the cell membranes after the synthesis using ultrasound and/or a homogenizer in order to destroy or cut up the cell membranes.

By using the method according to the present invention, one may achieve an effective, convenient, and inexpensive treatment of the near well bore region of the formation or the water leaking underground construction. In order to achieve sufficient sand consolidation, and thereby improved water tightness, it may be sufficient to carry out the method according to the present invention just once, using traditional pre-treatment of the near well bore region to be stabilized, or water leaking underground construction to be water tightened. The number of times which the method according to the invention, needs to be carried out depends among others on concentration and the amount of solution being injected. It is typically sufficient with less than ten repetitions of the method to obtain satisfying sand stabilizing. There might be some occasions where it is necessary to cool the near well bore region by pumping in sea or fresh water. In addition it may be an advantage to remove most of the oil in the region to be treated. In such cases, the region is flushed with diesel and a solvent that makes the porous region water wet, and then flushed with water to remove the solvent.

A method for consolidation according to the present invention, represents thus a significant improvement in relation to the priory known techniques, because supplied urease is stable and in solid form, and can be added to a solution prepared at the site of use. In general, such a method is environmentally friendly as only environmentally friendly chemicals are used; and the solutions have good moistening properties and very good penetration ability in porous, water wet materials.

The method according to the present invention, using urease in solid form, is important of logistic reasons since urease dissolved in a water based solution is unstable and cannot be stored more than 1 week before it starts to decompose. Pollutive bacteria might also cause reactions in the solution, making the urease in the solution inactive and therefore useless for the present application.

The amount of raw material needed for stabilization of an oil field formation, single well treatment, is of the order:

a) 1000-5000 kg *Canavalia* beans giving ~200-~1000 kg solid urease
b) 50-250 $m^3$ $Ca(NO_3)_2$ solution with $Ca^{2+}$ in the concentration range 0.25-2 Mol/l
c) 50-250 $m^3$ urea in the concentration range 0.25-2 Mol/l Example for Treating a Small to a Moderate Well:

From a water based mixture of 100 $m^3$ containing urea and $Ca^{2+}$ in concentrations 1 mol/l, and 2 gram/l lyophilized urease, 10.000 kg $CaCO_3$ will precipitate. This shows that a large amount of lyophilized urease is needed even for sand stabilization of moderate oil producing wells. The only way to get easy and rapid access to sufficient urease is therefore to store it in a solid form. The lyophilized urease should be dissolved in water the same day or no longer than 1-14 days depending on storage temperature, before it is to be used. A somewhat longer storage time may be obtained by adding chemicals preventing bacterial growth, as long as the chemicals are compatible with the $CaCO_3(s)$ precipitation process being a result of this invention without using lyophilized urease, the above example demands that a water-based solution of 50 $m^3$ containing up to 20 g/l beans has to be stirred 2-20 hrs, filtered (1000 kg *Canavalia* in 50 $m^3$ gives about 4 g/l urease) and transported to the site of use, where it has to be mixed with 50 $m^3$ of a solution containing 2 mol/l calcium and urea in order to create 100 $m^3$ of the active solution. This means, as stated above, that extraction of urease from beans in a water based solution for a simple well treatment has to be performed just ahead of each treatment. This process is of logistic reasons much less favourable than the process involving lyophilized urease. The main reason is that urease cannot be stored in the dissolved state more than a few days.

The method for production of solid urease represents thus a big improvement over the method represented by urease production immediately before it is to be used for the applications defined here.

Use of the method according to the present invention has two different applications with similar chemistries: 1) sand stabilization in oil field reservoirs and 2) water tightening of underground constructions, preferably oil field reservoirs. Sand stabilization and/or water tightening of oil field reservoirs should reduce the water production.

General features of the two technological applications needing large volumes of active solutions are that the method is environmentally friendly; the solutions have good water wetting properties and therefore good penetration properties in porous water wet material. The chemistry related to $CaCO_3$ precipitation is well described in Norwegian patent 326444 (Method and composition for stabilizing earth and sand to prevent soil erosion), incorporated herein in whole by reference, where the aim is to prevent soil erosion.

The present technology also include a controlled precipitation of $CaCO_3$ having the ability to bind sand and clay into a continuous matrix, which can stand the influence of external physical forces. $CaCO_3$ made by precipitation from urea, urease and $Ca^{2+}$ containing solutions have been suggested earlier as a method for sand stabilization oil well formations; SPE publication 50621 (Harris, R. E. and McKay, I. D. New application for enzymes in oil and gas production. The 1998 SPE European Petroleum Conference, The Hague, The Netherlands 20-22 Oct. 1998) and US patent No. 640181981.

There are several ways of obtaining a solution of urease in water, but some have more benefits than others. If the water based solution contains pollutants, such as certain heavy metals in concentrations above given limits, and certain anions such the phosphates, the precipitation will not give the desired compound, or even if the right compound precipitates, the sand will not consolidate. Zaborska et al (Zaborska W, Krajewska B and Olech Z, Heavy metal ions inhibition of jack bean urease: Potential for rapid contaminant probing. Journal of Enzyme Inhibition and Medicinal Chemistry 19:65-69 (2004)), investigated the effect of a series of heavy metals on the catalytic effect of urease in the urea decomposition. They found that some heavy metals like $Fe^{3+}$, $Cu^{2+}$, $Hg^{2+}$ reacted with urease and made it inactive. Phosphates added to the water solution in order to stabilize urease during its extraction from ordinary Jack Beans (*Canavalia ensiformis*) changed the morphology of the $CaCO_3$ formed, such that the sand consolidating properties of the compound disappeared. This effect is described in detail in Norwegian patent 326444.

Urease may also be deactivated by high $Ca^{2+}$ and urea concentrations. Thus it is important to keep both the $Ca^{2+}$ and urea concentrations in such a concentration range that the final $Ca^{2+}$ and/or urea concentrations never exceeds 1 mole/l when urease is present.

EXAMPLES

In the following the best way of providing solid urease, offering the most stable solution, at the lowest cost, and which gives the most efficient sand consolidation, is described.

*Canavalia* is a family of beans that comprises approximately 70-75 species of tropical origin, including Common Jack-bean (*Canavalia ensiformis*), Sword Bean (*Canavalia gladiata*) and *Canavalia cathartica*.

These beans are normally urease active and can therefore be used for urease extraction. The urease catalyst is prepared by extraction of 2-400 g raw material (eg. *Canavalia ensiformis*) dissolved in one liter water. The raw material is crushed or grounded to a particle distribution in the range 0.045<Average diameter/mm<0.5, before it is soaked in water and stirred for 2-20 hrs. The solid particles are removed by passing the solution through hydrocyclones and/or appropriate filters, the filtrate is lyophilized, and solid urease with impurities can be stored at temperatures below 4° C. for many months.

A preferred method for lyophilizing the filtrate of the filtered bean/water solution is to produce ice flakes by freezing the solution on a cooled rolling drum with a knife chipping the thin ice layer off the drum before it comes into contact with the solution again, or to produce an ice powder or granules by spray freezing. When frozen, the solid material is lyophilized.

Examples

Preparation of Solid Urease from Jack Beans

1. Laboratory Test.

Beans were milled on a Wiley mill using a 2 mm sieve. A solution was made by magnetically stirring 40 g milled bean in 1 liter distilled water, for 1 hour. Then the stirring was stopped, and filtering started. The solution was filtered twice using a water jet pump and a Blichner funnel, using first black ribbon filter paper (12-25 μm) and then blue ribbon (<2 μm). The filtration took some time, as some of the bean solutions contained glue-like material.

155 grams of filtered solution was frozen in a fridge (−4° C.) over night to avoid boiling and foaming in the lyophilizer when the vacuum pump was started. 24 hours was sufficient to remove the water, resulting in 1.35 g of pale yellow, fluffy powder. This powder dissolves readily in water and the $CaCO_3$ precipitation activity of the lyophilized material compared well with various water solutions of the same bean. See FIG. 3.

2. Industrial Test.

Urease active Jack Beans were used. They were first tested in order to show that they had the $CaCO_3$ precipitation activity as defined in FIG. 1

The industrial process was as follows:

The beans were crushed according to the size specifications given in the laboratory example above, and added to water in varying ratios; 1-100 g bean powder/1 liter water. The solution was soaking at occasional stirring 0.5-20 hrs at a temperature of 0-60 deg C., preferably 15-25 deg C., most preferred about 20 deg C., and then filtrated using pre-filtration and/or hydrocyclones, and then final filtration to obtain a substantially particle free solution (by visual observation).

The filtrate was continuously frozen onto a rotating steel drum cooled to between −200<T/° C.<−15. A knife was mounted so that the ice was lifted off the drum, producing ice flakes. The ice flakes were transferred into steel containers and lyophilized. The lyophilization process was run at a pressure close to technical vacuum and the temperature was kept in the range −100<T/° C.<+100, preferably 0<T/° C.<+60, most preferably about 50° C.

The final urease product was packed in waterproof plastic bags for storage at temperatures below 4° C.

The total productivity for this process using the beans-water ratio of 100 g beans in 1 liter of water is 18% (lyophilized urease powder/beans g/g*100%). The urease activity of this product was the best among all the trials with different water to beans ratios. The final product was tested for its $CaCO_3$ precipitation ability, and the results compared well with the results shown in FIG. 3.

3. Field Test, the Gullfaks Field in the North Sea

Urease solution was made and lyophilized as described in 2. The lyophilized urease was stored in the solid state ½ year. It was then dissolved in water, and injected into the near-well bore area of a well in the Gullfaks C field along with a calcium nitrate and a urea solution. After two consecutive injections of ~40 m³ of total solution with subsequent shut-in periods of 20 hours, the Gullfaks well was brought back on production with increased production rate without sand production problems.

The lyophilized solid product produced according to the present invention, is easy to handle, can be stored for long periods without becoming inactive, and can easily be brought to the location where it should be used, such as a well/underground construction. Before using the lyophilized urease for consolidation, it is either mixed into the $Ca^{2+}$ urea solution at the location where is should be used, or dissolved in water before it is mixed into the $Ca^{2+}$ urea solution and injected into the region to be treated.

The invention claimed is:

1. A method for water tightening of water bearing zones and stabilization of sand in underground constructions by introducing an aqueous salt solution comprising $Ca^{2+}$ ions, plant based urease and urea into said zones and constructions to precipitate at least one mineral, wherein the plant based urease is prepared in the absence of a pH buffer by a method comprising:
   (a) grounding the plant wherefrom the urease is based;
   (b) adding water to the ground plant;
   (c) soaking the ground plant in the water at occasional stirring between 2 and 20 h at room temperature to achieve a solution;
   (d) filtrating the achieved solution; and
   (e) lyophilizing the filtrate to achieve a lyophilized urease.

2. The method according to claim 1, characterized in that the lyophilized urease is mixed with water before it is added to the aqueous solution being introduced into the sand.

3. The method according to claim 2, characterized in that $Ca^{2+}$ and urea are in the same aqueous solution, and that the urease solution is added to the $Ca^{2+}$ and urea containing solution at the introduction into the construction, such that the concentration of the active components reach their target concentration in the construction to be treated.

4. The method according to claim 3, characterized in that the concentration of the active components reach target concentrations in the construction to be treated of 0.25-2 M $Ca^{2+}$ ions, 0.25-2 M urea and 0.5-6 g/l urease.

5. The method according to claim 1, characterized in that the plant wherefrom urease is achieved is beans, beans are ground to a powder, and water is added to the ground bean powder until the weight ratio bean powder to water is in the range 1:10-1:1000.

6. The method according to claim 5, characterized in that the bean is a *Canavalia*.

* * * * *